US005750647A

United States Patent [19]
Eyre et al.

[11] Patent Number: 5,750,647
[45] Date of Patent: May 12, 1998

[54] SYNTHETIC PEPTIDE ANALOGS OF NTX

[75] Inventors: David R. Eyre, Mercer Island; J. Daniel Clemens, Issaquah; Vincent W. Ochs, Seattle, all of Wash.

[73] Assignees: Washington Research Foundation; Ostex International, Inc., both of Seattle, Wash.

[21] Appl. No.: 446,206

[22] Filed: May 19, 1995

[51] Int. Cl.[6] .............................. C07K 7/00; C07K 7/06; G01N 33/53; G01N 33/531
[52] U.S. Cl. .................. 530/328; 530/356; 435/7.91; 435/7.93
[58] Field of Search ...................... 530/328, 356

[56] References Cited

U.S. PATENT DOCUMENTS

| | | | |
|---|---|---|---|
| 4,973,666 | 11/1990 | Eyre | 530/323 |
| 5,140,103 | 8/1992 | Eyre | 530/327 |
| 5,300,434 | 4/1994 | Eyre | 435/240.2 |
| 5,320,970 | 6/1994 | Eyre | 436/546 |

FOREIGN PATENT DOCUMENTS

WO 95/08115   3/1995   WIPO.

OTHER PUBLICATIONS

Hanson, et al., "A specific imunoassay for monitoring human bone resorption: quantitation of type I collagen cross–linked N–telopeptides in urine." *Journal of Bone and Mineral Research*, 7(11):1251–1258 (1992).

Bonde, Martin, et al., "Immunoassay for quantifying type I collagen degradation products in urine evaluated." *Clin Chem.*, 40(11):2022–2025, 1994.

*Primary Examiner*—Cecilia J. Tsang
*Assistant Examiner*—Michael Borin
*Attorney, Agent, or Firm*—Christensen O'Connor Johnson & Kindness PLLC

[57] ABSTRACT

Synthetic linear peptides embodied by Y-Tyr-Asp-Gly-X-Gly-Val-Gly (SEQ ID NO:1) which mimic the epitope recognized by mAb 1H11 (ATCC No. HB 10611) in cross-linked N-telopeptides of type I collagen (NTx).

14 Claims, No Drawings

SYNTHETIC PEPTIDE ANALOGS OF NTX

FIELD OF THE INVENTION

This invention relates to immunoassays and provides a synthetic peptide that acts as an immunoreactive analog of the natural cross-linked amino-terminal telopeptide of type I collagen.

BACKGROUND OF THE INVENTION

The following U.S. Patents are incorporated by reference: U.S. Pat. Nos. 4,973,666; 5,140,103; 5,300,434; and 5,320,970.

Cross-linked N-telopeptides of type I collagen (NTx) are excreted in urine as end-products of the process of bone resorption. These metabolites can be measured by immunoassay to provide an accurate and specific index of bone resorption activity, for example, using the monoclonal antibody (mAb) 1H11 produced by hybridoma 1H11. The hybridoma 1H11 was deposited on Nov. 20, 1990, at the American Type Culture Collection (ATCC), 12301 Parklawn Drive, Rockville, Md. 20852, U.S.A., under the provisions of the Budapest Treaty under Accession No. HB10611. The epitope recognized by mAb 1H11 is embodied in forms of the excreted cross-linked N-telopeptides that include the collagen α2(I) N-telopeptide sequence Gln-Tyr-Asp-Gly-K-Gly-Val-Gly, together with a linked second telopeptide from either α1(I) or α2(I), wherein K is embodied in the cross-link. The predominant cross-linked NTx metabolite excreted in urine is shown:

$$\text{Asp—Glu—K—Ser—Thr—Gly—Gly} \quad \alpha 1(I)$$
$$\text{Y—Tyr—Asp—Gly—K—Gly—Val—Gly} \quad \alpha 2(I)$$
$$\text{K}$$

wherein $$\text{K}$$
$$|$$
$$\text{K}$$
$$|$$
$$\text{K}$$

is hydroxylysyl pyridinoline or lysyl pyridinoline, and Y is glutamine (Gln or Q) or wholly cyclized pyrrolidone carboxylic acid (5-oxo-2-pyrrolidinecarboxylic acid, i.e., pyroglutamic acid) (J).

Linear peptides synthesized to match the human α1(1) or α2(1) N-telopeptide sequences, and in which K is simply lysine, are respectively not recognized or recognized very weakly by mAb 1H11.

SUMMARY OF THE INVENTION

Here we describe synthetic peptides that exhibit strong binding to mAb 1H11. The subject peptides are embodied by: Y-Tyr-Asp-Gly-X-Gly-Val-Gly (SEQ ID NO:1), wherein Y- is glutamine or pyrrolidone carboxylic acid, and wherein the structure of residue X is such that the peptide mimics features of the cross-linked NTx conformation and chemistry such that the peptide binds to mAb 1H11. In a first embodiment, X is: an amino acid residue with either a negatively charged, or a polar but uncharged, or a nonpolar side chain (R group). In a second embodiment, X bears a thiol group, in which case the peptides may dimerize via a cystine bridge. In a third embodiment, X bears an amino group that is conjugated to a carrier molecule or insoluble material. These molecular mimics of the cross-linked NTx epitope are conveniently synthesized for use as immunoassay standards, solid-phase coating antigens, immunogens, and other conjugated molecular structures for measuring NTx in biological samples.

DETAILED DESCRIPTION OF THE PREFERRED EMBODIMENT

The invention provides synthetic linear peptides which mimic the epitope recognized by mAb 1H11 in cross-linked NTx. The subject peptides are embodied by: Y-Tyr-Asp-Gly-X-Gly-Val-Gly, wherein the structure of residue X is such that the peptide mimics the NTx conformation and chemistry to the extent that the peptide binds to mab 1H11.

Starting with the observation that the synthesized α2(I) N-telopeptide sequence Gln-Tyr-Asp-Gly-Lys-Gly-Val-Gly (SEQ ID NO:2) is a very weak binding partner for mAb 1H11, a series of peptides was synthesized in which certain amino acids were substituted for lysine (Lys). Improved binding to mAb 1H11 was evident when the positively charged Lys residue was replaced with certain amino acids having negatively charged, polar, or nonpolar side chains (R groups). Replacement with amino acids having negatively charged side-chains, particularly glutamic acid (Glu) (SEQ ID NO:3) and to a lesser degree aspartic acid (Asp) (SEQ ID NO:4), or the polar cysteine (Cys) (SEQ ID NO:5), or the nonpolar norvaline (SEQ ID NO:6) improves the binding affinity dramatically. For example, the peptide Y-Tyr-Asp-Gly-Glu-Gly-Val-Gly (synthesized so that Y is pyroglutamic acid) had a binding affinity for mAb 1H11 comparable to that of the cross-linked NTx antigen. The mAb 1H11 inhibition curves for NTx (derived from either urine or bone) and Y-Tyr-Asp-Gly-Glu-Gly-Val-Gly are essentially parallel, indicating that the synthetic peptide mimics the natural epitope. Preferred embodiments of the subject synthetic peptides bind to mAb 1H11 at a substantially equimolar extent as does the cross-linked NTx metabolite (shown above) in antibody inhibition assays.

Available data suggest that the core sequence, Y-Tyr-Asp-Gly-X-Gly-Val-Gly, represents the maximum size for presenting the epitope recognized by mAb 1H11. Substituting Gly-Gly- (SEQ ID NO:7) for the N-terminal Y-, or adding -Gly-Leu to the C-terminus (SEQ ID NO:8), prevents mAb 1H11 binding. Determination of the minimum size of this core sequence can be routinely accomplished consistent with the following observations.

The degrees to which individual amino acids in the core sequence are considered essential for mAb 1H11, epitope binding are as follows. Preferential binding occurs when the N-terminal Y (position 1) is in the cyclized form (J), as occurs naturally in collagen chains. The Tyr residue in position 2 is an essential feature, as iodination of Tyr or substitution with Phe (SEQ ID NO:9) in this position blocks mAb 1H11 binding. The Asp residue in position 3 is also considered important, as substituents that eliminate the negative charge at this position block mAb 1H11 binding (based upon binding studies with NTx of modified structure from animal species other than human). Accordingly, Glu may be substituted for Asp in position 3 (SEQ ID NO:10). The Gly residue in position 4 is of unknown importance (e.g., substitution of Ala at this position (SEQ ID NO:11) might still afford substantial binding affinity). Equally, the Gly residues at positions 6 and 8 are of unascertained importance. The Val residue at position 7 is important, but it is likely that other hydrophobic substituents, such as Leu (SEQ ID NO:12) or Ile (SEQ ID NO:13), can maintain the requisite binding.

Accordingly, the invention provides, in a first embodiment, a peptide that binds to mAb 1H11, comprising Y-Tyr-Asp-Gly-X-Gly-Val-Gly (SEQ ID NO:14), wherein Y is glutamine or pyrrolidone carboxylic acid, and X is an amino acid with either a negatively charged R group, or a polar but uncharged R group, or a nonpolar (hydrophobic) R group.

A suitable amino acid with a negatively charged R group is selected from among Glu, Asp, and other natural and synthetic α-amino acids which bear a negatively charged R group such as a carboxyl, sulfate, or phosphate group. A representative example is α-aminoadipic acid (SEQ ID NO:15).

A suitable amino acid with a polar but uncharged R group is selected from among Asn (SEQ ID NO:16), Cys, Gln (SEQ ID NO:17), Ser (SEQ ID NO:18), Thr (SEQ ID NO:19), Tyr (SEQ ID NO:20), and other natural and synthetic α-amino acids which bear a polar but uncharged R group such as characterize Asn, Cys, Gln, Gly, Ser, Thr, and Tyr. Representative examples include pyridinylalanine (SEQ ID NO:21) (Bachem) and other α-amino acids wherein the R group has a pyridine ring (SEQ ID NO:22). Cysteine and other thiol bearing α-amino acids are particularly preferred embodiments in terms of the degree of mAb 1H11 binding.

A suitable amino acid with a nonpolar R group is selected from among Ala (SEQ ID NO:23), Ile (SEQ ID NO:24), Met (SEQ ID NO:25), Pro (SEQ ID NO:26), Val, Trp (SEQ ID NO:31), norvaline, and other natural and synthetic α-amino acids which bear a nonpolar R group such as characterize Ala, Ile, Leu, Met, Phe, Pro, Trp, and Val. Norvaline is presently preferred.

In a second embodiment, the invention provides a peptide that binds to mAb 1H11, comprising Y-Tyr-Asp-Gly-X-Gly-Val-Gly (SEQ ID NO:28), wherein Y is glutamine or pyrrolidone carboxylic acid, and X is an α-amino acid bearing a thiol group. In the presence of atmospheric oxygen this peptide forms disulfide-bonded dimers that mimic the NTx epitope as follows:

```
Y—Tyr—Asp—Gly—X₁—Gly—Val—Gly
              |
              S
              |
              S
              |
Y—Tyr—Asp—Gly—X₂—Gly—Val—Gly.
```

Each of residues $X_1$ and $X_2$ may be the same or a different α-amino acid bearing a side chain (R) with a thiol group. Representative examples (X) include cysteine, homocysteine (SEQ ID NO:29), and related residues in which R contains 0-3 carbon atoms.

In a third embodiment, the natural epitope embodied in urinary NTx is mimicked by conjugating the synthetic peptide Y-Tyr-Asp-Gly-X-Gly-Val-Gly (SEQ ID NO:30), wherein X is an α-amino acid bearing a side chain amino group (for example, lysine with an epsilon amino group), through the amino group, for example by glutaraldehyde using standard procedures, to either a solute or an insoluble material. Alternatively, X is an α-amino acid bearing a side chain thiol group. Representative X residues for this purpose are lysine and cysteine, respectively, and representative linking agents, for conjugation to, e.g., bovine serum albumin, are glutaraldehyde and m-malieimidobenzoyl-N-hydroxysuccinimide ester (MBS). By solute is meant a molecular substance dissolved in aqueous solution. Representive solutes for this purpose include proteins, such as keyhole limpet hemocyanin (KLH), albumin, and enzymes, peptides such as Y-Tyr-Asp-Gly-Cys-Gly-Val-Gly (or Y-Tyr-Asp-Gly-Lys-Gly-Val-Gly), and other soluble molecules such as biotin, avidin, and fluorescent and chemiluminescent moieties. Representative insoluble materials include latex particles, dipsticks, microtiter wells, and other substrata used in heterogeneous immunoassays. Once conjugated by such, a standard linking agent to, for example, KLH the antibody-binding affinity of the Y-Tyr-Asp-Gly-Lys-Gly-Val-Gly structure for an antibody (e.g., mAb 1H11) that recognizes NTx from urine or bone is increased about 50-fold, approximating the binding affinity of the natural epitope. Such a conjugate can be used in solution as a competing antigen or as a coating agent for solid surfaces, for example, to coat wells in a microtiter-plate kit or latex or other particles in automated assay systems.

Accordingly, this third embodiment of the invention provides a conjugated peptide that binds to mAb 1H11, comprising:

```
Y—Tyr—Asp—Gly—X—Gly—Val—Gly
              |
              R
``` wherein X is an amino acid residue bearing an amino group or thiol group and R is either a solute or an insoluble material conjugated through the amino group or thiol group to residue X.

In summary, the invention provides synthetic peptides that mimic the complex epitope of cross-linked human bone and urinary NTx recognized immunochemically, for example, by mAb 1H11. These synthetic peptides can be used to simplify the manufacture of immunoassay kits and other commercial formats, so as to provide reproducible standards for calibration and novel synthetic antigen formulations, for use for example in homogeneous immunoassay systems such as disclosed in U.S. Pat. Nos. 5,212,064 and 5,362,625 (Microgenics Corporation) and other automated assay systems.

While the preferred embodiment of the invention has been illustrated and described, it will be appreciated that various changes can be made therein without departing from the spirit and scope of the invention.

---

The embodiments of the invention in which an exclusive property or privilege is claimed are defined as follows:

1. A peptide that binds to mAb 1H11, comprising:

Y-Tyr-Asp-Gly-X-Gly-Val-Gly (SEQ ID NO:14)

wherein Y is glutamine or pyrrolidone carboxylic acid, and X is an α-amino acid residue with either a negatively charged R group, or a polar but uncharged R group, or a nonpolar R group.

2. The peptide of claim 1, wherein X is an α-amino acid residue with a negatively charged R group selected from among the group of amino acids consisting of Glu (SEQ ID NO:3) and Asp (SEQ ID NO:4).

3. The peptide of claim 2, wherein X is Glu (SEQ ID NO:3).

4. The peptide of claim 1, wherein X is Cys (SEQ ID NO:5).

5. The peptide of claim 1, wherein X is an amino acid residue with an R group which comprises a pyridine ring (SEQ ID NO:22).

6. The peptide of claim 1, wherein X is an α-amino acid residue with a nonpolar R group selected from among the group of amino acids consisting of Pro (SEQ ID NO:26), Trp (SEQ ID NO:31), and norvaline (SEQ ID NO:6).

7. The peptide of claim 6, wherein X is norvaline (SEQ ID NO:6).

8. A peptide that binds to mAb 1H11, comprising:

Y-Tyr-Asp-Gly-X-Gly-Val-Gly (SEQ ID NO:28)

wherein Y is glutamine or pyrrolidone carboxylic acid, and X is an α-amino acid bearing a thiol group.

9. The peptide of claim 8, wherein X is cysteine (SEQ ID NO:5) or homocysteine (SEQ ID NO:29).

10. A peptide that binds to mAb 1H11, comprising:

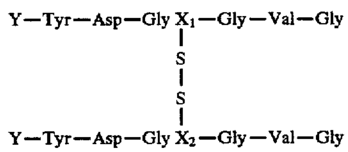

wherein Y is glutamine or pyrrolidone carboxylic acid, and $X_1$ and $X_2$ are α-amino acid residues.

11. The peptide of claim 10, wherein $X_1$-S and $X_2$-S are independently selected from among cysteine and homocysteine residues.

12. A peptide that binds to mAb 1H11, comprising:

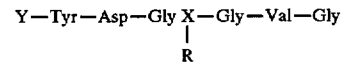

wherein Y is glutamine or pyrrolidone carboxylic acid, X is an α-amino acid residue bearing an amino or thiol group, and R is a solute conjugated through the amino or thiol group to X.

13. The peptide of claim 12, wherein the solute is a protein or peptide.

14. A peptide that binds to mAb 1H11, comprising:

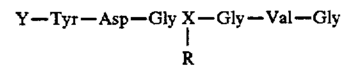

wherein Y is glutamine or pyrrolidone carboxylic acid, X is an amino acid residue bearing an amino or thiol group, and R is an insoluble material conjugated through the amino or thiol group to X.

* * * * *

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( B ) LOCATION: 1
        ( D ) OTHER INFORMATION: Xaa is glutamine or pyrrolidone
            carboxylic acid.

( i x ) FEATURE:
        ( B ) LOCATION: 5
        ( D ) OTHER INFORMATION: Xaa is an amino acid residue with
            either a negatively charged, or a polar but
            uncharged, or a nonpolar side chain (R group);
            or Xaa bears a thiol group; or Xaa bears an amino
            group that is conjugated to a carrier molecule or
            insoluble material.

( x i ) SEQUENCE DESCRIPTION: SEQ ID NO:1:

```
Xaa  Tyr  Asp  Gly  Xaa  Gly  Val  Gly
 1                    5
```

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:2:

```
Gln  Tyr  Asp  Gly  Lys  Gly  Val  Gly
 1                    5
```

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( B ) LOCATION: 1
        ( D ) OTHER INFORMATION: Xaa is glutamine or pyrrolidone
            carboxylic acid.

( x i ) SEQUENCE DESCRIPTION: SEQ ID NO:3:

```
Xaa  Tyr  Asp  Gly  Glu  Gly  Val  Gly
 1                    5
```

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
    ( B ) LOCATION: 1
    ( D ) OTHER INFORMATION: Xaa is glutamine or pyrrolidone carboxylic acid.

( x i ) SEQUENCE DESCRIPTION: SEQ ID NO:4:

Xaa Tyr Asp Gly Asp Gly Val Gly
1               5

( 2 ) INFORMATION FOR SEQ ID NO:5:

( i ) SEQUENCE CHARACTERISTICS:
    ( A ) LENGTH: 8 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: N-terminal ( i x ) FEATURE:
    ( B ) LOCATION: 1
    ( D ) OTHER INFORMATION: Xaa is glutamine or pyrrolidone carboxylic acid.

( x i ) SEQUENCE DESCRIPTION: SEQ ID NO:5:

Xaa Tyr Asp Gly Cys Gly Val Gly
1               5

( 2 ) INFORMATION FOR SEQ ID NO:6:

( i ) SEQUENCE CHARACTERISTICS:
    ( A ) LENGTH: 8 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: N-terminal ( i x ) FEATURE:
    ( B ) LOCATION: 1
    ( D ) OTHER INFORMATION: Xaa is glutamine or pyrrolidone carboxylic acid.

( i x ) FEATURE:
    ( B ) LOCATION: 5
    ( D ) OTHER INFORMATION: Xaa is norvaline.

( x i ) SEQUENCE DESCRIPTION: SEQ ID NO:6:

Xaa Tyr Asp Gly Xaa Gly Val Gly
1               5

( 2 ) INFORMATION FOR SEQ ID NO:7:

( i ) SEQUENCE CHARACTERISTICS:
    ( A ) LENGTH: 9 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: N-terminal ( i x ) FEATURE:
    ( B ) LOCATION: 6

( D ) OTHER INFORMATION: Xaa is an amino acid with either a
negatively charged R group, or a polar but uncharged
R group, or a nonpolar (hydrophobic) R group.

( x i ) SEQUENCE DESCRIPTION: SEQ ID NO:7:

Gly Gly Tyr Asp Gly Xaa Gly Val Gly
1               5

( 2 ) INFORMATION FOR SEQ ID NO:8:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( B ) LOCATION: 1
        ( D ) OTHER INFORMATION: Xaa is glutamine or pyrrolidone
carboxylic acid.

( i x ) FEATURE:
        ( B ) LOCATION: 5
        ( D ) OTHER INFORMATION: Xaa is an amino acid with either a
negatively charged R group, or a polar but uncharged
R group, or a nonpolar (hydrophobic) R group.

( x i ) SEQUENCE DESCRIPTION: SEQ ID NO:8:

Xaa Tyr Asp Gly Xaa Gly Val Gly Gly Leu
1               5                   10

( 2 ) INFORMATION FOR SEQ ID NO:9:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( B ) LOCATION: 1
        ( D ) OTHER INFORMATION: Xaa is glutamine or pyrrolidone
carboxylic acid.

( i x ) FEATURE:
        ( B ) LOCATION: 5
        ( D ) OTHER INFORMATION: Xaa is an amino acid with either a
negatively charged R group, or a polar but uncharged
R group, or a nonpolar (hydrophobic) R group.

( x i ) SEQUENCE DESCRIPTION: SEQ ID NO:9:

Xaa Phe Asp Gly Xaa Gly Val Gly
1               5

( 2 ) INFORMATION FOR SEQ ID NO:10:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
    ( B ) LOCATION: 1
    ( D ) OTHER INFORMATION: Xaa is glutamine or pyrrolidone
        carboxylic acid.

( i x ) FEATURE:
    ( B ) LOCATION: 5
    ( D ) OTHER INFORMATION: Xaa is an amino acid with either a
        negatively charged R group, or a polar but uncharged
        R group, or a nonpolar (hydrophobic) R group.

( x i ) SEQUENCE DESCRIPTION: SEQ ID NO:10:

```
Xaa  Tyr  Glu  Gly  Xaa  Gly  Val  Gly
1                    5
```

( 2 ) INFORMATION FOR SEQ ID NO:11:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( B ) LOCATION: 1
        ( D ) OTHER INFORMATION: Xaa is glutamine or pyrrolidone
            carboxylic acid.

( i x ) FEATURE:
        ( B ) LOCATION: 5
        ( D ) OTHER INFORMATION: Xaa is an amino acid with either a
            negatively charged R group, or a polar but uncharged
            R group, or a nonpolar (hydrophobic) R group.

( x i ) SEQUENCE DESCRIPTION: SEQ ID NO:11:

```
Xaa  Tyr  Asp  Ala  Xaa  Gly  Val  Gly
1                    5
```

( 2 ) INFORMATION FOR SEQ ID NO:12:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( i x ) FEATURE:
        ( B ) LOCATION: 1
        ( D ) OTHER INFORMATION: Xaa is glutamine or pyrrolidone
            carboxylic acid.

( i x ) FEATURE:
        ( B ) LOCATION: 5
        ( D ) OTHER INFORMATION: Xaa is an amino acid with either a
            negatively charged R group, or a polar but uncharged
            R group, or a nonpolar (hydrophobic) R group.

( x i ) SEQUENCE DESCRIPTION: SEQ ID NO:12:

```
Xaa  Tyr  Asp  Gly  Xaa  Gly  Leu  Gly
1                    5
```

( 2 ) INFORMATION FOR SEQ ID NO:13:

( i ) SEQUENCE CHARACTERISTICS:
        ( A ) LENGTH: 8 amino acids
        ( B ) TYPE: amino acid (C) STRANDEDNESS:
(D) TOPOLOGY: linear (i i) MOLECULE TYPE: peptide (v) FRAGMENT TYPE: N-terminal (i x) FEATURE:
(B) LOCATION: 1
(D) OTHER INFORMATION: Xaa is glutamine or pyrrolidone carboxylic acid.

(i x) FEATURE:
(B) LOCATION: 5
(D) OTHER INFORMATION: Xaa is an amino acid with either a negatively charged R group, or a polar but uncharged R group, or a nonpolar (hydrophobic) R group.

(x i) SEQUENCE DESCRIPTION: SEQ ID NO:13:

Xaa Tyr Asp Gly Xaa Gly Ile Gly
1               5

(2) INFORMATION FOR SEQ ID NO:14:

(i) SEQUENCE CHARACTERISTICS:
(A) LENGTH: 8 amino acids
(B) TYPE: amino acid
(C) STRANDEDNESS:
(D) TOPOLOGY: linear (i i) MOLECULE TYPE: peptide (v) FRAGMENT TYPE: N-terminal (i x) FEATURE:
(B) LOCATION: 1
(D) OTHER INFORMATION: Xaa is glutamine or pyrrolidone carboxylic acid.

(i x) FEATURE:
(B) LOCATION: 5
(D) OTHER INFORMATION: Xaa is an amino acid with either a negatively charged R group, or a polar but uncharged R group, or a nonpolar (hydrophobic) R group.

(x i) SEQUENCE DESCRIPTION: SEQ ID NO:14:

Xaa Tyr Asp Gly Xaa Gly Val Gly
1               5

(2) INFORMATION FOR SEQ ID NO:15:

(i) SEQUENCE CHARACTERISTICS:
(A) LENGTH: 8 amino acids
(B) TYPE: amino acid
(C) STRANDEDNESS:
(D) TOPOLOGY: linear (i i) MOLECULE TYPE: peptide (v) FRAGMENT TYPE: N-terminal (i x) FEATURE:
(B) LOCATION: 1
(D) OTHER INFORMATION: Xaa is glutamine or pyrrolidone carboxylic acid.

(i x) FEATURE:
(B) LOCATION: 5
(D) OTHER INFORMATION: Xaa is alpha-aminoadipic acid.

(x i) SEQUENCE DESCRIPTION: SEQ ID NO:15:

Xaa Tyr Asp Gly Xaa Gly Val Gly
1               5

( 2 ) INFORMATION FOR SEQ ID NO:16:

( i ) SEQUENCE CHARACTERISTICS:
　　　　　　　　( A ) LENGTH: 8 amino acids
　　　　　　　　( B ) TYPE: amino acid
　　　　　　　　( C ) STRANDEDNESS:
　　　　　　　　( D ) TOPOLOGY: linear ( i i ) MOLECULE TYPE: peptide ( v ) FRAGMENT TYPE: N-terminal ( i x ) FEATURE:
　　　　　　　　( B ) LOCATION: 1
　　　　　　　　( D ) OTHER INFORMATION: Xaa is glutamine or pyrrolidone
　　　　　　　　　　carboxylic acid.

( x i ) SEQUENCE DESCRIPTION: SEQ ID NO:16:

Xaa　Tyr　Asp　Gly　Asn　Gly　Val　Gly
1　　　　　　　　　　5

( 2 ) INFORMATION FOR SEQ ID NO:17:

( i ) SEQUENCE CHARACTERISTICS:
　　　　　　　　( A ) LENGTH: 8 amino acids
　　　　　　　　( B ) TYPE: amino acid
　　　　　　　　( C ) STRANDEDNESS:
　　　　　　　　( D ) TOPOLOGY: linear ( i i ) MOLECULE TYPE: peptide ( v ) FRAGMENT TYPE: N-terminal ( i x ) FEATURE:
　　　　　　　　( B ) LOCATION: 1
　　　　　　　　( D ) OTHER INFORMATION: Xaa is glutamine or pyrrolidone
　　　　　　　　　　carboxylic acid.

( x i ) SEQUENCE DESCRIPTION: SEQ ID NO:17:

Xaa　Tyr　Asp　Gly　Gln　Gly　Val　Gly
1　　　　　　　　　　5

( 2 ) INFORMATION FOR SEQ ID NO:18:

( i ) SEQUENCE CHARACTERISTICS:
　　　　　　　　( A ) LENGTH: 8 amino acids
　　　　　　　　( B ) TYPE: amino acid
　　　　　　　　( C ) STRANDEDNESS:
　　　　　　　　( D ) TOPOLOGY: linear ( i i ) MOLECULE TYPE: peptide ( v ) FRAGMENT TYPE: N-terminal ( i x ) FEATURE:
　　　　　　　　( B ) LOCATION: 1
　　　　　　　　( D ) OTHER INFORMATION: Xaa is glutamine or pyrrolidone
　　　　　　　　　　carboxylic acid.

( x i ) SEQUENCE DESCRIPTION: SEQ ID NO:18:

Xaa　Tyr　Asp　Gly　Ser　Gly　Val　Gly
1　　　　　　　　　　5

( 2 ) INFORMATION FOR SEQ ID NO:19:

( i ) SEQUENCE CHARACTERISTICS:
　　　　　　　　( A ) LENGTH: 8 amino acids
　　　　　　　　( B ) TYPE: amino acid
　　　　　　　　( C ) STRANDEDNESS:
　　　　　　　　( D ) TOPOLOGY: linear ( i i ) MOLECULE TYPE: peptide ( v ) FRAGMENT TYPE: N-terminal ( i x ) FEATURE:
   ( B ) LOCATION: 1
   ( D ) OTHER INFORMATION: Xaa is glutamine or pyrrolidone carboxylic acid.

( x i ) SEQUENCE DESCRIPTION: SEQ ID NO:19:

Xaa Tyr Asp Gly Thr Gly Val Gly
1               5

( 2 ) INFORMATION FOR SEQ ID NO:20:

( i ) SEQUENCE CHARACTERISTICS:
      ( A ) LENGTH: 8 amino acids
      ( B ) TYPE: amino acid
      ( C ) STRANDEDNESS:
      ( D ) TOPOLOGY: linear ( i i ) MOLECULE TYPE: peptide ( v ) FRAGMENT TYPE: N-terminal ( i x ) FEATURE:
      ( B ) LOCATION: 1
      ( D ) OTHER INFORMATION: Xaa is glutamine or pyrrolidone carboxylic acid.

( x i ) SEQUENCE DESCRIPTION: SEQ ID NO:20:

Xaa Tyr Asp Gly Tyr Gly Val Gly
1               5

( 2 ) INFORMATION FOR SEQ ID NO:21:

( i ) SEQUENCE CHARACTERISTICS:
      ( A ) LENGTH: 8 amino acids
      ( B ) TYPE: amino acid
      ( C ) STRANDEDNESS:
      ( D ) TOPOLOGY: linear ( i i ) MOLECULE TYPE: peptide ( v ) FRAGMENT TYPE: N-terminal ( i x ) FEATURE:
      ( B ) LOCATION: 1
      ( D ) OTHER INFORMATION: Xaa is glutamine or pyrrolidone carboxylic acid.

( i x ) FEATURE:
      ( B ) LOCATION: 5
      ( D ) OTHER INFORMATION: Xaa is pyridinylalanine.

( x i ) SEQUENCE DESCRIPTION: SEQ ID NO:21:

Xaa Tyr Asp Gly Xaa Gly Val Gly
1               5

( 2 ) INFORMATION FOR SEQ ID NO:22:

( i ) SEQUENCE CHARACTERISTICS:
      ( A ) LENGTH: 8 amino acids
      ( B ) TYPE: amino acid
      ( C ) STRANDEDNESS:
      ( D ) TOPOLOGY: linear ( i i ) MOLECULE TYPE: peptide ( v ) FRAGMENT TYPE: N-terminal ( i x ) FEATURE:
      ( B ) LOCATION: 1
      ( D ) OTHER INFORMATION: Xaa is glutamine or pyrrolidone carboxylic acid.

( i x ) FEATURE:

(B) LOCATION: 5
(D) OTHER INFORMATION: Xaa is an alpha-amino acid wherein the
R group has a pyridine ring.

(x i) SEQUENCE DESCRIPTION: SEQ ID NO:22:

Xaa Tyr Asp Gly Xaa Gly Val Gly
1               5

(2) INFORMATION FOR SEQ ID NO:23:

(i) SEQUENCE CHARACTERISTICS:
   (A) LENGTH: 8 amino acids
   (B) TYPE: amino acid
   (C) STRANDEDNESS:
   (D) TOPOLOGY: linear (ii) MOLECULE TYPE: peptide (v) FRAGMENT TYPE: N-terminal (ix) FEATURE:
   (B) LOCATION: 1
   (D) OTHER INFORMATION: Xaa is glutamine or pyrrolidone
      carboxylic acid.

(x i) SEQUENCE DESCRIPTION: SEQ ID NO:23:

Xaa Tyr Asp Gly Ala Gly Val Gly
1               5

(2) INFORMATION FOR SEQ ID NO:24:

(i) SEQUENCE CHARACTERISTICS:
   (A) LENGTH: 8 amino acids
   (B) TYPE: amino acid
   (C) STRANDEDNESS:
   (D) TOPOLOGY: linear (ii) MOLECULE TYPE: peptide (v) FRAGMENT TYPE: N-terminal (ix) FEATURE:
   (B) LOCATION: 1
   (D) OTHER INFORMATION: Xaa is glutamine or pyrrolidone
      carboxylic acid.

(x i) SEQUENCE DESCRIPTION: SEQ ID NO:24:

Xaa Tyr Asp Gly Ile Gly Val Gly
1               5

(2) INFORMATION FOR SEQ ID NO:25:

(i) SEQUENCE CHARACTERISTICS:
   (A) LENGTH: 8 amino acids
   (B) TYPE: amino acid
   (C) STRANDEDNESS:
   (D) TOPOLOGY: linear (ii) MOLECULE TYPE: peptide (v) FRAGMENT TYPE: N-terminal (ix) FEATURE:
   (B) LOCATION: 1
   (D) OTHER INFORMATION: Xaa is glutamine or pyrrolidone
      carboxylic acid.

(x i) SEQUENCE DESCRIPTION: SEQ ID NO:25:

Xaa Tyr Asp Gly Met Gly Val Gly
1               5

(2) INFORMATION FOR SEQ ID NO:26:

( i ) SEQUENCE CHARACTERISTICS:
  ( A ) LENGTH: 8 amino acids
  ( B ) TYPE: amino acid
  ( C ) STRANDEDNESS:
  ( D ) TOPOLOGY: linear ( i i ) MOLECULE TYPE: peptide ( v ) FRAGMENT TYPE: N-terminal ( i x ) FEATURE:
  ( B ) LOCATION: 1
  ( D ) OTHER INFORMATION: Xaa is glutamine or pyrrolidone carboxylic acid.

( x i ) SEQUENCE DESCRIPTION: SEQ ID NO:26:

Xaa Tyr Asp Gly Pro Gly Val Gly
1                 5

( 2 ) INFORMATION FOR SEQ ID NO:27:

( i ) SEQUENCE CHARACTERISTICS:
    ( A ) LENGTH: 8 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: N-terminal ( i x ) FEATURE:
    ( B ) LOCATION: 1
    ( D ) OTHER INFORMATION: Xaa is glutamine or pyrrolidone carboxylic acid.

( x i ) SEQUENCE DESCRIPTION: SEQ ID NO:27:

Xaa Tyr Asp Gly Val Gly Val Gly
1                 5

( 2 ) INFORMATION FOR SEQ ID NO:28:

( i ) SEQUENCE CHARACTERISTICS:
    ( A ) LENGTH: 8 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: N-terminal ( i x ) FEATURE:
    ( B ) LOCATION: 1
    ( D ) OTHER INFORMATION: Xaa is Gln is glutamine or pyrrolidone carboxylic acid.

( i x ) FEATURE:
    ( B ) LOCATION: 5
    ( D ) OTHER INFORMATION: Xaa is an alpha-amino acid bearing a thiol group.

( x i ) SEQUENCE DESCRIPTION: SEQ ID NO:28:

Xaa Tyr Asp Gly Xaa Gly Val Gly
1                 5

( 2 ) INFORMATION FOR SEQ ID NO:29:

( i ) SEQUENCE CHARACTERISTICS:
    ( A ) LENGTH: 8 amino acids
    ( B ) TYPE: amino acid
    ( C ) STRANDEDNESS:
    ( D ) TOPOLOGY: linear (i i) MOLECULE TYPE: peptide (v) FRAGMENT TYPE: N-terminal (i x) FEATURE:
 (B) LOCATION: 1
 (D) OTHER INFORMATION: Xaa is glutamine or pyrrolidone carboxylic acid.

(i x) FEATURE:
 (B) LOCATION: 5
 (D) OTHER INFORMATION: Xaa is homocysteine.

(x i) SEQUENCE DESCRIPTION: SEQ ID NO:29:

Xaa Tyr Asp Gly Xaa Gly Val Gly
1               5

(2) INFORMATION FOR SEQ ID NO:30:

(i) SEQUENCE CHARACTERISTICS:
 (A) LENGTH: 8 amino acids
 (B) TYPE: amino acid
 (C) STRANDEDNESS:
 (D) TOPOLOGY: linear (i i) MOLECULE TYPE: peptide (v) FRAGMENT TYPE: N-terminal (i x) FEATURE:
 (B) LOCATION: 1
 (D) OTHER INFORMATION: Xaa is glutamine or pyrrolidone carboxylic acid.

(i x) FEATURE:
 (B) LOCATION: 5
 (D) OTHER INFORMATION: Xaa is an alplha-amino acid bearing a side chain amino group or a side chain thiol group.

(x i) SEQUENCE DESCRIPTION: SEQ ID NO:30:

Xaa Tyr Asp Gly Xaa Gly Val Gly
1               5

(2) INFORMATION FOR SEQ ID NO:31:

(i) SEQUENCE CHARACTERISTICS:
 (A) LENGTH: 8 amino acids
 (B) TYPE: amino acid
 (C) STRANDEDNESS:
 (D) TOPOLOGY: linear (i i) MOLECULE TYPE: peptide (v) FRAGMENT TYPE: N-terminal (i x) FEATURE:
 (B) LOCATION: 1
 (D) OTHER INFORMATION: Xaa is glutamine or pyrrolidone carboxylic acid.

(x i) SEQUENCE DESCRIPTION: SEQ ID NO:31:

Xaa Tyr Asp Gly Trp Gly Val Gly
1               5